United States Patent
Peera et al.

(10) Patent No.: US 9,605,163 B2
(45) Date of Patent: Mar. 28, 2017

(54) AMINOALCOHOL COMPOUNDS AND THEIR USE AS ZERO OR LOW VOC ADDITIVES FOR PAINTS AND COATINGS

(75) Inventors: Asghar Peera, Cary, IL (US); Raymond J. Swedo, Mount Prospect, IL (US); G. David Green, Cary, IL (US); Esin G. Busche, Naperville, IL (US); John W. Quinn, Skokie, IL (US); Shreyas Bhide, Mumbai (IN); Mahesh Sawant, Pune (IN)

(73) Assignee: ANGUS CHEMICAL COMPANY, Buffalo Grove, IL (US)

( * ) Notice: Subject to any disclaimer, the term of this patent is extended or adjusted under 35 U.S.C. 154(b) by 26 days.

(21) Appl. No.: 14/127,405

(22) PCT Filed: Jul. 23, 2012

(86) PCT No.: PCT/US2012/047819
§ 371 (c)(1),
(2), (4) Date: Dec. 18, 2013

(87) PCT Pub. No.: WO2013/016270
PCT Pub. Date: Jan. 31, 2013

(65) Prior Publication Data
US 2014/0130714 A1     May 15, 2014

Related U.S. Application Data

(60) Provisional application No. 61/512,631, filed on Jul. 28, 2011.

(30) Foreign Application Priority Data

Apr. 3, 2012   (IN) ............................. 1342CHE2012

(51) Int. Cl.
| C01B 25/00 | (2006.01) |
| C09D 7/12 | (2006.01) |
| C07C 215/12 | (2006.01) |
| C09D 5/14 | (2006.01) |
| A01N 25/04 | (2006.01) |
| A01N 33/08 | (2006.01) |
| C07C 215/14 | (2006.01) |
| C07C 217/28 | (2006.01) |

(52) U.S. Cl.
CPC ........... C09D 7/1233 (2013.01); A01N 25/04 (2013.01); A01N 33/08 (2013.01); C07C 215/12 (2013.01); C07C 215/14 (2013.01); C07C 217/28 (2013.01); C09D 5/14 (2013.01)

(58) Field of Classification Search
CPC ........ C09D 7/002; C09D 7/1233; C09D 5/14; A01N 25/04; A01N 33/08
USPC .................................................. 106/287.26
See application file for complete search history.

(56) References Cited

U.S. PATENT DOCUMENTS

| 2,393,825 A | 8/1942 | Senkus |
| 2,403,344 A * | 7/1946 | De Groote .................. 554/110 |
| 2,878,144 A | 3/1957 | Conbere et al. |
| 3,535,294 A | 10/1970 | Marumo et al. |
| 3,657,183 A | 4/1972 | Strefanski |
| 4,083,872 A | 4/1978 | Schwarze et al. |
| 4,259,219 A | 3/1981 | Eschwey et al. |
| 4,281,201 A | 7/1981 | Abend |
| 4,497,933 A | 2/1985 | Gorzinski et al. |
| 4,732,691 A | 3/1988 | Wirth et al. |
| 5,336,784 A | 8/1994 | Hiskey et al. |
| 5,370,731 A | 12/1994 | Yamashita et al. |
| 6,656,977 B2 | 12/2003 | Slone et al. |
| 7,393,887 B2 | 7/2008 | Friedrich et al. |
| 7,871,602 B2 | 1/2011 | Dassanayake et al. |
| 8,575,396 B2 | 11/2013 | Tomlinson et al. |
| 2003/0032698 A1 | 2/2003 | Smith et al. |
| 2004/0054043 A1 | 3/2004 | Friedrich et al. |
| 2005/0079984 A1 | 4/2005 | Miles |
| 2007/0179227 A1 | 8/2007 | Sugerman |
| 2009/0218224 A1 * | 9/2009 | Weber ........................ 204/548 |
| 2010/0041801 A1 | 2/2010 | Dowling et al. |

(Continued)

FOREIGN PATENT DOCUMENTS

| DE | 40 03 662 | 8/1991 |
| EP | 0 459 692 | 12/1991 |

(Continued)

OTHER PUBLICATIONS

Communication on European Patent Application 12741230.2, mailed Jan. 24, 2014.
First Office Action on Chinese Application 201280037563.7, mailed Sep. 3, 2014.
International Preliminary Report on Patentability for PCT/US2012/047819, issued Jan. 28, 2014.

(Continued)

*Primary Examiner* — Kaj K Olsen
*Assistant Examiner* — Alexander Polyansky
(74) *Attorney, Agent, or Firm* — Foley & Lardner LLP

(57) ABSTRACT

Provided are aminoalcohol compounds for use as additives for paints and coatings. The compounds are of the formula (I): wherein x, R, $R^1$, $R^2$, $R^3$, $R^4$, $R^5$, $R^6$, and $R^A$ are as defined herein.

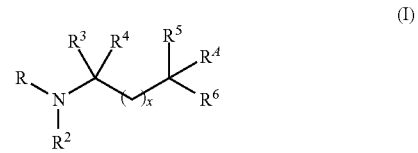

20 Claims, No Drawings

(56) References Cited

U.S. PATENT DOCUMENTS

| | | | |
|---|---|---|---|
| 2010/0280165 A1* | 11/2010 | Terrenoire et al. | 524/502 |
| 2011/0146536 A1* | 6/2011 | Tomlinson | C07C 215/08 106/287.22 |
| 2012/0116126 A1 | 5/2012 | Ruppin et al. | |

FOREIGN PATENT DOCUMENTS

| | | |
|---|---|---|
| EP | 0 601 219 | 6/1994 |
| EP | 0 691 327 | 1/1996 |
| JP | 49-005449 | 1/1974 |
| JP | 50-023065 | 8/1975 |
| JP | 54-147937 | 11/1979 |
| JP | 54-163829 | 12/1979 |
| JP | 61-143342 | 7/1986 |
| JP | 63-148260 | 6/1988 |
| JP | 06-271450 | 9/1994 |
| JP | 2006-171357 | 6/2006 |
| JP | 2010-254838 | 11/2010 |
| WO | WO-91/02037 | 2/1991 |
| WO | WO-97/38968 | 10/1997 |
| WO | WO-00/06678 | 2/2000 |

OTHER PUBLICATIONS

International Search Report on PCT/US2012/047819, mailed Nov. 14, 2012.
Non-Final Office Action on U.S. Appl. No. 14/127,403, mailed Sep. 30, 2014.
Senkus, Reaction of Primary Aliphatic Amines with Formaldehyde and Nitroparaffins, Journal of the American Chemical Society, vol. 68, pp. 10-12, 1946.
Bonningue, et al. Phosphoranes by Ring Closure. IV. Some Examples of Bicyclic Chiral Phosphoranes, 1979. Abstract Only.
Lawrence, et al., Metal-Directed Synthesis of the New Potentially Pentadentate Aminoalcohol Ligand 5-Amino-5-Methyl-3, 7-Diazanonan-1, 9-Diol Based on Ethanolamine, Polyhedron, vol. 7, No. 14, pp. 1263-1266, 1988.
Moriguchi, et al., Simple Method of Calculating Octanol/Water Partition Coefficient, Chemical and Pharmaceutical Bulletin, vol. 40, Issue 1, pp. 1237-130, 1992.
Oh, et al., Structure and phosphodiesterase Activity of Bis-Tris coordinated Tanthanide (III) complexes, Chemical Communications, vol. 20, pp. 2189-2190, 1998.
Wu, et al. Sulfoxygenation catalysed by oxidovanadium complexes, European Journal of Inorganic Chemistry, vol. 2008, Issue 33, pp. 5203-5213, 2008.
Morikawa et al., A new Class of Nitrosources. VIII. Chemical & Pharmaceutical Bulletin, 1983, vol. 31, No. 5, pp. 1646-1651.
Mousseron et al., Alicyclic Series. XIX. Amino Alcohols Bulletin de lay Society Chimique de France, 1947, pp. 850-868 (English translation not available).
Notice of Reasons for Rejection issued on Japanese Application 2014-522927, mailed Dec. 1, 2015.
Registry (STN) Online—Searched on Sep. 18, 2015, 8 pages.
Zaitsev et al., "Titanium Complexes of Dialkanolamine Ligands: Synthesis and Structure," European Journal of Inorganic Chemistry, 2006, vol. 10, pp. 1987-1999.

* cited by examiner

AMINOALCOHOL COMPOUNDS AND THEIR USE AS ZERO OR LOW VOC ADDITIVES FOR PAINTS AND COATINGS

CROSS REFERENCE TO RELATED APPLICATIONS

This application is a 35 USC §371 national phase filing of PCT/US2012/047819 filed Jul. 23, 2012, which claims priority from U.S. provisional application Ser. No. 61/512,631, filed Jul. 28, 2011, and from Indian application serial number 1342/CHE/2012, filed Apr. 3, 2012, which are incorporated herein by reference.

BACKGROUND

This invention relates generally to aminoalcohol compounds and their use as low odor, zero or low volatile organic content (VOC) additives for paints and coatings.

Organic amines are used in aqueous based paints as neutralizing agents. In many geographies, paint manufacturers are facing regulations to reduce the volatile organic content (VOC) of their formulations. Most conventional neutralizing amines are 100% volatile and are therefore VOC contributors. In addition, when used in an otherwise low VOC paint formulation, the odor of such amines is more noticeable.

Ammonia and inorganic hydroxides and carbonates are potential alternatives for use as neutralizers, that are by definition non-VOC contributors. However, ammonia, while an efficient neutralizer, has a very strong odor and is therefore unsuitable for use in low odor paint. Inorganic hydroxides and carbonates are undesirable because they often result in coatings with poor scrub resistance.

Paints and coatings are often subjected to widely varying temperatures, for instance during storage and transportation. Such varying temperatures may result in the paint or coating undergoing one or more freeze-thaw cycles. Freezing and thawing, however, has a detrimental effect on paint and coatings, unfavorably affecting their performance (e.g., by increasing the viscosity), and sometimes rendering the formulations unusable. Simple glycols (e.g., ethylene glycol) are sometimes included in paints and coatings with the purpose of providing freeze-thaw (F/T) stability. However, these materials may not be desirable because they may be of high VOC and therefore generally not suitable for use in low VOC formulations.

The problem addressed by this invention is the provision additives for paints and coatings which exhibit low or no VOC and may further have very low or no amine odor.

STATEMENT OF INVENTION

We have now found that aminoalcohol compounds of the structures represented below function as highly efficient additives for paints and coatings. for instance, the compounds function as highly efficient neutralizers, and/or as freeze thaw stabilizers. In addition, the compounds may possess a number of other favorable properties that further enhance their applicability in paints and coatings. Advantageously the compounds exhibit either low or no VOC and in some embodiments, very low amine odor.

In one aspect, there is provided a compound of formula I:

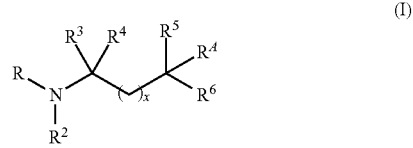

wherein x is 0, 1, or 2;
$R^A$ is OH or alkyl;
R is $CH_2CHR^1OH$, and $R^1$ is H, alkyl, cycloalkyl, phenyl, phenyl-alkyl-, alkoxyalkyl-, or hydroxyalkyl;
$R^2$ is H, alkyl, cycloalkyl, hydroxyalkyl, or independently R;
$R^3$ and $R^4$ are independently H, alkyl, cycloalkyl, phenyl, or hydroxyalkyl, or $R^3$ and $R^4$, together with the carbon to which they are attached, form cycloalkyl; and
$R^5$ and $R^6$ are independently H or alkyl, or $R^5$ and $R^6$, together with the carbon to which they are attached, form cycloalkyl,
or, when x is 0, $R^3$ and $R^5$, together with the carbon atoms to which they are attached, form cycloalkyl;
provided that when x is 0, $R^A$ is OH and when x is 1 or 2, $R^A$ is alkyl.

In another aspect, there is provided an aqueous based paint or coating comprising an additive, a binder, a carrier, and a pigment, wherein the additive is a compound of formula I:

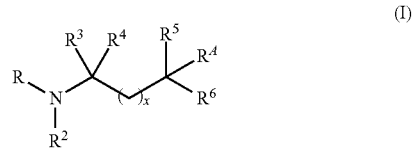

wherein x is 0, 1, or 2;
$R^A$ is OH or alkyl;
R is $CH_2CHR^1OH$, and $R^1$ is H, alkyl, cycloalkyl, phenyl, phenyl-alkyl-, alkoxyalkyl-, or hydroxyalkyl;
$R^2$ is H, alkyl, cycloalkyl, hydroxyalkyl, or independently R;
$R^3$ and $R^4$ are independently H, alkyl, cycloalkyl, phenyl, or hydroxyalkyl, or $R^3$ and $R^4$, together with the carbon to which they are attached, form cycloalkyl; and
$R^5$ and $R^6$ are independently H or alkyl, or $R^5$ and $R^6$, together with the carbon to which they are attached, form cycloalkyl,
or, when x is 0, $R^3$ and $R^5$, together with the carbon atoms to which they are attached, form cycloalkyl;
provided that when x is 0, $R^A$ is OH and when x is 1 or 2, $R^A$ is alkyl.

In a further aspect, there is provided a method for reducing the volatile organic compound content of an aqueous based paint or coating that contains a neutralizing agent or freeze-thaw additive, a binder, a carrier, and a pigment, the method comprising using as the neutralizing agent or freeze-thaw additive a compound of formula I as described herein.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

"Low-VOC formulation" and like terms mean an organic volatile content of 50 grams or less per liter of paint (water excluded) for the entire paint or coating formulation. "Zero-VOC formulation" and like terms mean an organic volatile content of 5 grams or less per liter of paint (water excluded) for the entire paint or coating formulation. Total organic volatile content may be calculated by using information for the individual raw materials. Organic volatile content of raw materials (other than the aminoalcohol compounds of the invention) may be measured using well known tests, such as the EPA24 test method.

"Zero or low VOC compound" and like terms mean that a particular aminoalcohol compound of the invention passes the criteria set forth by one or more gas chromatography methods, such as ASTM D6886-rev method, ISO 11890 or GB 18581. ASTM D6886-rev method is preferred.

"Alkyl," as used in this specification, whether alone or as part of another group (e.g., in dialkylamino), encompasses straight and branched chain aliphatic groups having 1-10, alternatively 1-8, or alternatively 1-6 alkyl carbon atoms. Preferred alkyl groups include, without limitation, methyl, ethyl, propyl, isopropyl, butyl, isobutyl, sec-butyl, tert-butyl, pentyl, and hexyl. Unless otherwise indicated, the alkyl group is optionally substituted with 1, 2, or 3, preferably 1 or 2, more preferably 1, substituents that are compatible with the syntheses described herein. Such substituents include, but are not limited to, nitro, halogen, ester, nitrile, amide, carboxylic acids (e.g., $C_0$-$C_6$—COOH), and $C_2$-$C_6$ alkene. Unless otherwise indicated, the foregoing substituent groups are not themselves further substituted.

"Hydroxyalkyl" refers to an alkyl group, as defined above, that contains a hydroxy substituent on one of its carbons, either a terminal or an internal carbon. Preferred hydroxyalkyl include 2-hydroxyethyl-, and hydroxymethyl. Hydroxymethyl is more preferred.

The term "alkoxy" refers to a saturated straight or branched chain alkoxy group containing 1 to 6 carbon atoms (e.g. methoxy, ethoxy, n-propoxy, iso-propoxy, n-butoxy, iso-butoxy, sec-butoxy, tert-butoxy, n-pentoxy, neopentyloxy, iso-pentyloxy, n-hexyloxy or iso-hexyloxy), and preferably 1 to 4 carbon atoms. Representative examples of preferred alkoxy groups include methoxy, ethoxy, n-propoxy, iso-propoxy, n-butoxy, iso-butoxy, sec-butoxy and tert-butoxy.

The term "alkoxyalkyl" refers to an alkyl group, as defined above, wherein one hydrogen atom has been replaced by an alkoxy group. Examples of alkoxyalkyl groups include, but are not limited to, 3-methoxy-propyl, methoxymethyl and 2-methoxy-ethyl.

The term "cycloalkyl" refers to saturated and partially unsaturated cyclic hydrocarbon groups having 3 to 12 ring carbon atoms, alternatively 3 to 8 ring carbon atoms, or alternatively 3 to 7 ring carbon atoms. Preferred cycloalkyl groups include, without limitation, cyclopropyl, cyclobutyl, cyclopentyl, cyclopentenyl, cyclohexyl, cyclohexenyl, cycloheptyl, and cyclooctyl. Unless otherwise indicated, the cycloalkyl group is optionally substituted with 1, 2, or 3, preferably 1 or 2, more preferably 1, substituents that are compatible with the syntheses described herein. Such substituents include, but are not limited to, alkyl, nitro, halogen, ester, nitrile, amide, carboxylic acids (e.g., $C_0$-$C_6$—COOH), and $C_2$-$C_6$ alkene. A preferred substituent is alkyl.

An "aryl" group is a C6-C14 aromatic moiety comprising one to three aromatic rings. Preferably, the aryl group is a C6-C12, alternatively C6-C10 aryl group. Preferred aryl include, without limitation, phenyl, naphthyl, anthracenyl, and fluorenyl. More preferred are phenyl and naphthyl. Further preferred is phenyl. Unless otherwise indicated, the aryl group is optionally substituted with 1, 2, or 3, preferably 1 or 2, more preferably 1, substituents that are compatible with the syntheses described herein. Such substituents include, but are not limited to, $C_1$-$C_6$ alkyl, nitro, halogen, ester, nitrile, amide, carboxylic acids (e.g., $C_0$-$C_6$—COOH), and $C_2$-$C_6$ alkene. Unless otherwise indicated, the foregoing substituent groups are not themselves further substituted.

The term "aryl-alkyl-" refers to aryl-$C_1$-$C_{10}$ alkyl-. A preferred aryl-alkyl group is benzyl.

"Glycol-free" and like terms mean that a paint formulation comprises less than 1 wt %, preferably less than 0.5 wt % and more preferably less than 0.2 wt %, of a glycol based on the weight of the formulation. The paint or coating formulation of this invention can comprise some minimal amount, i.e., less than 1 wt %, of glycol for purposes other than as a freeze-thaw agent, but this amount is insufficient to impart to the formulation sufficient freeze-thaw properties so as to pass the 5-cycle F/T test described in the Examples, infra.

"Octanol-water partition coefficient ($K_{OW}$)" is a dimensionless concentration ratio whose magnitude expresses the distribution of a compound between equal volumes of two partially miscible solvents, n-octanol and water after they have reached equilibrium. The higher the $K_{OW}$, the more non-polar the compound. Log $K_{OW}$ values are generally inversely related to aqueous solubility and directly proportional to molecular weight.

As noted above, in one aspect the invention provides aminoalcohol compounds that are useful as additives for aqueous-based paint and coating formulations. For instance, in some embodiments, the aminoalcohol compounds function as neutralizing agents in paints or coatings. Neutralizing agents are included in such formulations to raise the pH to a desired value, typically between 7 and 13, more typically between 8 and 10. Most conventional neutralizing agents currently used in the industry are VOC contributors. In addition, when used in an otherwise low VOC formulation, the odor of conventional neutralizing agents is more noticeable.

In contrast, the aminoalcohol compounds of the invention are excellent low odor materials with the benefit of having zero or low VOC. In addition to their excellent low VOC and low odor attributes, the aminoalcohol compounds may impart comparable performance properties to those provided by conventional neutralizing amines. Consequently, the advantages of low odor and low VOC are achieved with the aminoalcohol compounds of the invention, without significant negative impact on other attributes of the paint or coating.

Alternatively, or in addition, to functioning as neutralizing agents, compounds of the invention are useful as F/T additives or agents. Freeze thaw additives (stabilizers) are added to paint and coating formulations to depress the freezing point and therefore to allow the formulations to maintain their desired properties, including viscosity, even after exposure to temperature variation, particularly temperatures that would cause freezing and thawing. When such additives are absent, the paint may flocculate and/or have increased viscosity which may make them difficult to use. In some cases, formulations may solidify, rendering them unusable. The compounds of the invention provide freeze-thaw stability enhancement with the added benefit of being low or no VOC materials. Thus, the compounds are effective replacements for higher VOC freeze-thaw additives, such as glycols.

Further, the aminoalcohol compounds of the invention may enhance (improve or provide attributes comparable to commercial materials such as 2-amino-2-methyl-1-propanol) various other desirable properties to paints and coatings, in addition to neutralization and freeze thaw stabilization, such as one or more of the following: corrosion resistance, scrub resistance, blocking resistance, codispersion, gloss enhancement, color acceptance and stability, reduced yellowing, aging stability, water resistance, washability, stain resistance, low temperature coalescence and synergy for microbial control.

The aminoalcohol compounds of the invention are of the formula I:

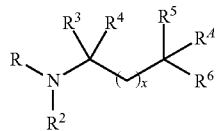

wherein x, R, $R^1$, $R^2$, $R^3$, $R^4$, $R^5$, $R^6$, and $R^A$ are as defined above.

In some embodiments, the aminoalcohol compounds of formula I are compounds of formula I-1, which are compounds of formula I wherein x is 0 and $R^3$ and $R^4$ are independently hydroxyalkyl, preferably both are hydroxymethyl.

In some embodiments, the compounds of formula I are of the formula I-2, which are compounds of formula I wherein x is 0 and $R^3$ and $R^4$ are independently alkyl, preferably independently $C_{1-3}$ alkyl, or preferably both are methyl.

In some embodiments, the compounds of formula I are of the formula I-3, which are compounds of formula I wherein x is 0, $R^3$ is alkyl, preferably $C_{1-3}$ alkyl, or preferably methyl, and $R^4$ is hydroxyalkyl, preferably hydroxymethyl.

In some embodiments, the compounds of formula I are of the formula I-4, which are compounds of formula I wherein x is 0 and $R^3$ and $R^4$ are both H.

In some embodiments, the compounds of formulae I, I-1, I-2, I-3, and I-4 are of the formula I-5, which are compounds of formula I, I-1, I-2, I-3, or I-4 wherein $R^5$ and $R^6$ are both H.

In some embodiments, the compounds of formula I are of the formula I-6, which are compounds of formula I wherein x is 0 and $R^3$ and $R^5$, together with the carbon atoms to which they are attached, form cycloalkyl. In some embodiments, they form cyclohexyl.

In some embodiments, the compounds of formula I are of the formula I-7, which are compounds of formula I wherein x is 1 or 2 and $R^3$, $R^4$, $R^5$, and $R^6$ are independently alkyl. In some embodiments of formula I-7, and $R^3$, $R^4$, $R^5$, and $R^6$ are independently $C_1$-$C_3$ alkyl. In some embodiments, $R^3$, $R^4$, $R^5$, and $R^6$ are each methyl.

In some embodiments, the compound of formulae I, I-1, I-2, I-3, I-4, I-5, I-6 and I-7 are of the formula I-8, which are compounds of formula I, I-1, I-2, I-3, I-4, I-5, I-6 or I-7 wherein $R^2$ is H.

In some embodiments, the compound of formulae I, I-1, I-2, I-3, I-4, I-5, I-6 and I-7 are of the formula I-9, which are compounds of formula I, I-1, I-2, I-3, I-4, I-5, I-6 or I-7 wherein R and $R^2$ are both $CH_2CHR^1OH$.

In some embodiments, the compound of formulae I, I-1, I-2, I-3, I-4, I-5, I-6 and I-7 are of the formula I-10, which are compounds of formula I, I-1, I-2, I-3, I-4, I-5, I-6 or I-7 wherein R and $R^2$ are both $CH_2CHR^1OH$ and $R^1$ at both occurrences is simultaneously H or simultaneously alkyl (preferably $C_1$-$C_3$ alkyl, more preferably ethyl or methyl).

In some embodiments, the compound of formulae I, I-1, I-2, I-3, I-4, I-5, I-6 and I-7 are of the formula I-11, which are compounds of formula I, I-1, I-2, I-3, I-4, I-5, I-6 or I-7 wherein R is $CH_2CHR^1OH$, $R^1$ is alkoxyalkyl (preferably isopropoxymethyl) and $R^2$ is H.

In some embodiments, the aminoalcohols are compounds as shown in Table 1.

TABLE 1

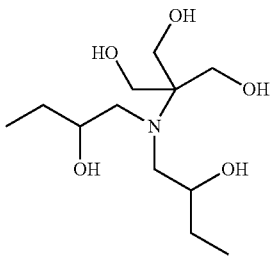 [SMILES: CCC(O)CN(CC(O)CC)C(CO)(CO)CO]

TA-2BO
2-(bis(2-hydroxybutyl)amino)-2-(hydroxymethyl)propane-1,3-diol

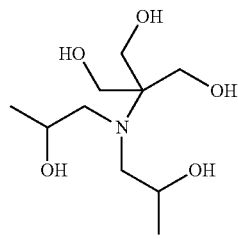 [SMILES: CC(O)CN(CC(C)O)C(CO)(CO)CO]

TA-2PO
2-(bis(2-hydroxypropyl)amino)-2-(hydroxymethyl)propane-1,3-diol

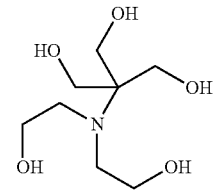 [SMILES: OCCN(CCO)C(CO)(CO)CO]

TA-2EO
2-(bis(2-hydroxyethyl)amino)-2-(hydroxymethyl)propane-1,3-diol

TABLE 1-continued

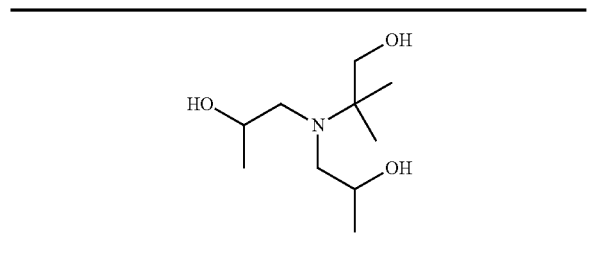

AMP-2PO
1,1'-((1-hydroxy-2-methylpropan-2-yl)azanediyl)bis(propan-2-ol)

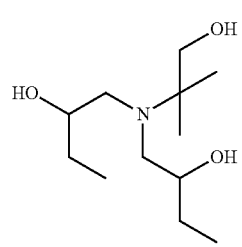 [SMILES: CCC(O)CN(CC(O)CC)C(C)(C)CO]

AMP-2BO
1,1'-((1-hydroxy-2-methylpropan-2-yl)azanediyl)bis(butan-2-ol)

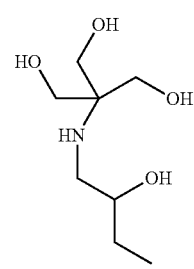

TA-1BO
2-((2-hydroxybutyl)amino)-2-(hydroxymethyl)propane-1,3-diol

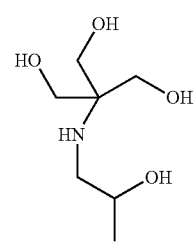

TA-1PO
2-(hydroxymethyl)-2-((2-hydroxypropyl)amino)propane-1,3-diol

TABLE 1-continued

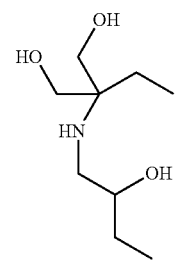

AEPD-1BO
2-ethyl-2-((2-hydroxybutyl)amino)propane-1,3-diol

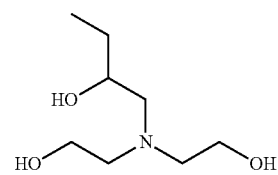

DEA-1BO
2,2'-((2-hydroxybutyl)azanediyl)diethanol

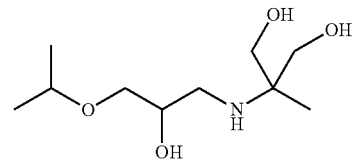

AMPD-IPM)
2-((2-hydroxy-3-isopropoxypropyl)amino)-2-methylpropane-1,3-diol

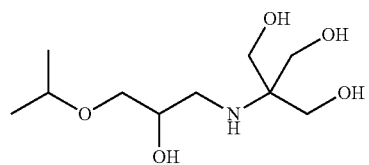 [SMILES: CC(C)OCC(O)CNC(CO)(CO)CO]

TA-IPM
2-((2-hydroxy-3-isopropoxypropyl)amino)-2-(hydroxymethyl)propane-1,3-diol

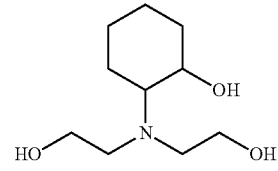 [SMILES: OCCN(CCO)C1CCCCC1O]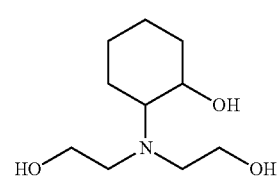

DEA-CyHO
2,2'-((2-hydroxy-cyclohexyl)azanediyl)diethanol

TABLE 1-continued

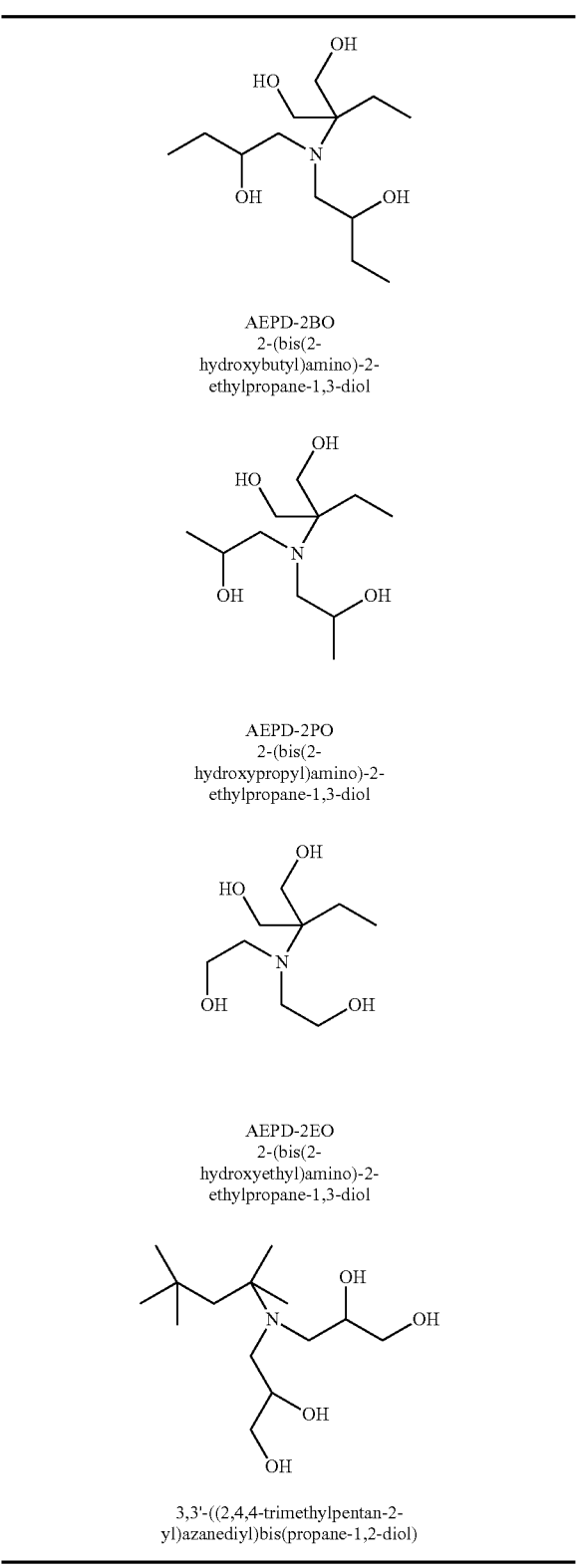

AEPD-2BO
2-(bis(2-hydroxybutyl)amino)-2-ethylpropane-1,3-diol

AEPD-2PO
2-(bis(2-hydroxypropyl)amino)-2-ethylpropane-1,3-diol

AEPD-2EO
2-(bis(2-hydroxyethyl)amino)-2-ethylpropane-1,3-diol 3,3'-((2,4,4-trimethylpentan-2-yl)azanediyl)bis(propane-1,2-diol)

In some embodiments, 2,2'-((2-hydroxycyclohexyl)azanediyl)diethanol is excluded as a compound of the invention.

The compounds of formula I may be readily prepared. An example of a typical procedure is shown in Scheme I.

SCHEME I

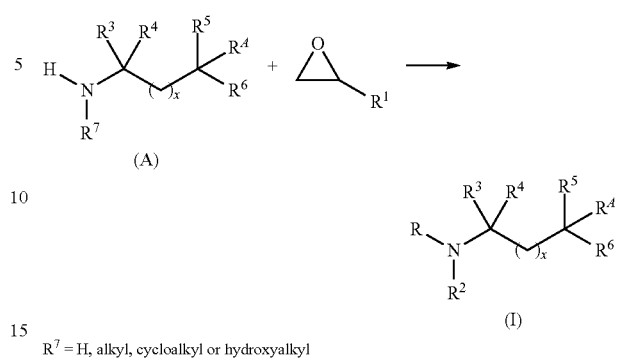

$R^7$ = H, alkyl, cycloalkyl or hydroxyalkyl

As shown in Scheme 1, compounds of the invention may be prepared by reacting an amine of formula A with one or more alkylene or arylene oxide compounds. In an typical procedure, the alkylene or arylene oxide is slowly added to the stirred formula A amine. The reaction may be conducted neat, or using a solvent, such as water or alcohol (e.g., methanol), particularly if the reaction material is viscous and unable to stir. The reaction may be carried at varying temperature, such as between room temperature and 100° C. In some embodiments, it is preferred to maintain the temperature between about 40 and 60° C. After addition of the alkylene or arylene oxide, the reaction may be stirred at room temperature for sufficient time until it reaches the desired level of completion, such as 2 to 24 hours. The product mixture may be used as is, particularly if the reaction is run neat, or may be further purified by known methods.

Formula A amines are commercially available and/or may be readily synthesized by those skilled in the art. Examples of suitable formula A amines include, without limitation: tris(hydroxymethyl)aminomethane; 2-amino-2-methyl-1-propanol; 2-amino-2-methyl-1,3-propanediol; 2-amino-2-ethyl-1,3-propanediol; diethanolamine; and 2,4,4-trimethyl-2-pentanamine.

Similarly, alkylene oxides are commercially available or may be easily prepared. Non-limiting examples of suitable alkylene oxides include: ethylene oxide; propylene oxide; butylene oxide; (isopropoxymethyl)oxirane; glycidol; styrene oxide; and cyclohexene epoxide.

The compounds of the invention are useful as additives for aqueous-based paint and coating formulations. Thus in a further aspect, the invention provides an aqueous based paint or coating in which a compound of formula I is present as an additive. In some embodiments, the paint or coating formulation containing the compound of formula I is overall a low VOC, alternatively a zero VOC, formulation. The paint or coating is used to provide a protective and/or decorative barrier for residential and industrial surfaces, such as for floors, automobiles, exteriors and interiors of houses, and other buildings. The paint or coating formulation, in addition to comprising an additive compound of formula I, also comprises a binder, a pigment, and a carrier.

Pigments are included to provide hiding power and the desired color to the final coated material and may also be used to provide bulk to the paint or coating. While multiple pigments may be present in end-use paints or coatings, sometimes only white pigment, such as titanium oxide, perhaps in combination with extender pigments such as calcium carbonate and/or kaolin clay, is added in the early stages of the formation of the formulation. Any other desired pigments of various colors (including more white pigment) can optionally be added at the later stages of, or after, the formulation is completed.

Pigments may be organic or inorganic. Examples of pigments can include, but are not limited to, titanium dioxide, kaolin clay, calcined kaolin clay, carbon black, iron oxide black, iron oxide yellow, iron oxide red, iron oxide brown, organic red pigments, including quinacridone red and metallized and non-metallized azo reds (e.g., lithols, lithol rubine, toluidine red, naphthol red), phthalocyanine blue, phthalocyanine green, mono- or di-arylide yellow, benzimidazolone yellow, heterocyclic yellow, quinacridone magenta, quinacridone violet, and the like, and any combination thereof. In some embodiments, the amount of pigment may be from 10 to 30% by weight based on the total weight of the formulation.

Binders are included in the paint and coating formulations to provide a network in which the pigment particles are dispersed and suspended. Binders bind the pigment particles together and provide integrity and adhesion for the paint or coating film. Generally, for aqueous based paints and coatings, the binders are latex based materials.

Latex binders are typically prepared by free radical initiated aqueous emulsion polymerization of a monomer mixture containing alkyl acrylate (methyl acrylate, ethyl acrylate, butyl acrylate and/or 2-ethylhexylacrylate), alkyl methacrylate, vinyl alcohol/acetate, styrene, and/or acrylonitrile and ethylene type monomers. Suitable binders include acrylic, vinyl acrylic, styrenated-acrylic, vinyl acetate ethylene based materials, or blends of these materials. The amount of the binder in the formulations of the invention can be the amount conventionally used in paint and coating formulations, which can vary widely due to the desired gloss/sheen range, and also the solids concentration, of a specific paint formulation. By way of non-limiting example, the amount of binder solids can be from about 5% to about 35% by weight of the total formulation weight.

The formulations also contain a carrier in which the formulation ingredients are dissolved, dispersed, and/or suspended. In the aqueous based formulations of the invention, the carrier is usually water, although other water-based solutions such as water-alcohol mixtures and the like may be used. The aqueous carrier generally makes up the balance of the formulation, after all the other ingredients have been accounted for.

Other materials may be included in the paint and coating formulations besides the additives, pigments, binders, and carriers discussed above. These include, but are not limited to, leveling agents and surfactants, thickeners, rheology modifiers, co-solvents such as glycols, including propylene glycol or ethylene glycol, corrosion inhibitors, defoamers, co-dispersants, additional aminoalcohol compounds, bases, and biocides.

The paint and coating formulations of the invention may be manufactured by conventional paint manufacturing techniques, which are well known to those skilled in the art. Typically, the formulations are manufactured by a two-step process. First, a dispersion phase, commonly referred to as the grind phase, is prepared by mixing the dry pigments with other grind phase components, including most other solid powder formulation materials, under constant high shear agitation to provide a high viscosity and high solids mixture. This part of the process is designed to effectively wet and dis-agglomerate the dry pigments and stabilize them in an aqueous dispersion.

The second step of the paint manufacturing process is commonly referred to as the letdown or thindown phase, because the viscous grind is diluted with the remaining formulation components, which are generally less viscous than the grind mix. Typically, the binders, any predispersed pigments, and any other paint materials that only require mixing and perhaps moderate shear, are incorporated during the letdown phase. The letdown phase may be done either by sequentially adding the letdown components into a vessel containing the grind mix, or by adding the grind mix into a vessel containing a premix of the latex resins and other letdown components, followed by sequential addition of the final letdown components. In either case, constant agitation is needed, although application of high shear is not required.

The compounds of formula I of the invention are typically added to the formulation at one or more of three different places in the manufacturing process: to the pigment dispersion, to the binder dispersion, and/or in a final addition to the paint formulation. The amount used may be readily determined by person of ordinary skill in the art.

For instance, when present as a neutralizer, it may be preferable to use an amount that is determined based on the desired pH of the formulation. Typically, an amount of the compound is added so as to provide a final pH in the range of 7 to 13, preferably 8 to 10, more preferably about 8.5 to 9.5. In some embodiments, an inorganic base may be included in the formulation as a co-neutralizer with the compound of formula I. An example of a suitable base is sodium hydroxide (NaOH). In some embodiments, the weight ratio of compound of formula I to inorganic base is from 3:1 to 1:3, alternatively 2:1 to 1:2, or alternatively it is 1:1.

When used as a freeze-thaw additive, the compounds are preferably added late in the formulation (e.g., during the letdown phase of the manufacturing process, as described above). In some embodiments, the compounds of the invention function primarily as a freeze-thaw stabilizer. When used primarily as a freeze-thaw stabilizer, the amount of the compound is, in some embodiments, from about 0.2% to about 10%, based on total weight of the formulation.

In a further aspect, the invention provides a method for reducing the volatile organic compound content of an aqueous based paint or coating that contains a neutralizing agent and/or freeze-thaw stabilizer, a binder, a carrier, and a pigment. The method comprises using as the neutralizing agent and/or freeze-thaw stabilizer an effective amount of a compound of formula (I).

As noted above, the compounds of the invention function as zero or low VOC and low odor additives for aqueous based paints and coating formulations. For instance, the compounds may function as neutralizers and/or as freeze-thaw (F/T) stabilizers. Because of their ability to function as freeze thaw stabilizers, known F/T stabilizers, such as glycols, may be eliminated from paints and coating formulations. This has the advantage of potentially further reducing the VOC of a formulation.

Thus, in a still further aspect the invention provides a glycol-free, low VOC paint or coating formulation comprising a compound of formula I. For use as a F/T stabilizer, it is preferred for the compound of formula I to have the following attributes: the total number of amine groups (primary, secondary and tertiary) is 1 to 10; the number of hydroxy groups (—OH) is of 1 to 20; and the octanol-water partition coefficient is from −10 to 10.

In some embodiments, a glycol-free, low VOC paint or coating formulation of the invention may comprise in weight percent (wt %) based on the weight of the formulation:

5-35% of a binder; 10-30% pigment; 0.2 to 10% compound of formula I; and 30-60% carrier. In some embodiments, the pH of the formulation is in a range between 7 and 13. In some embodiments, 3,3'-((2,4,4-trimethylpentan-2-yl)azanediyl)bis(propane-1,2-diol) is a preferred F/T stabilizer.

In addition to neutralization and freeze-thaw stabilization, the compounds of the invention may enhance various other desirable properties to the formulation, such as one or more of the following: corrosion resistance, scrub resistance, blocking resistance, codispersion, gloss enhancement, color acceptance and stability, reduced yellowing, aging stability, water resistance, washability, stain resistance, low temperature coalescence, and synergy with biocides present in the formulation for microbial control.

Some embodiments of the invention will now be described in detail in the following Examples.

EXAMPLES

Generic Experimental

Synthesis. A 3-neck round bottom flask equipped with a magnetic stirrer, nitrogen blanket, thermocouple controlled heating mantle and addition funnel is charged with desired amine (1.0 equivalent) The addition funnel is charged with desired alkylene oxides (1 or more equivalents). The reaction is run neat and if the material is viscous and unable to stir, solvent such as water or alcohol can be used. During the addition, the reaction temperature is maintained at ca. 25-100° C. A mild exotherm is noted at the beginning of the addition for alkyl oxides such as propylene oxide and butylene oxide. However, a large exotherm may be observed when glycidol is used as the epoxide. The exotherm is controlled by slow addition and/or ice bath. After completing the addition, the reaction is stirred at room temperature for 2-24 hrs. The material may be used as-is in the paint application.

pKa. pKa values are determined by titration using 0.5 $NH_2SO_4$ as titrant with water as solvent. Duplicate analyses are performed.

VOC. VOC properties are tested according to the ASTM D6886-rev method. The parameters used are as shown in Table 2:

TABLE 2

| Parameters | ASTM 6886-rev |
| --- | --- |
| Column | DB-5, 30 m × 0.25 mm, 1 μm |
| Flow Rate (ml/min) | 1.0 ml/min |
| Inlet Temp (C.) | 260 |
| Detector Temp (C.) | 270 |
| Initial Temp (C.) | 50 |
| Hold (min) | 4 |
| Rate1 (C./min) | 20 |
| Final Temp1 (C.) | 250 |
| Hold (min) | 6 |
| Rate 2 (C./min) | 20 |
| Total time (min) | 20 |
| Marker | None |
| Column Material | 5% Phenyl/95% Methylpolysiloxane |

Example 1

Synthesis, pKa, and VOC Evaluation of 3,3'-((2,4,4-trimethylpentan-2-yl)azanediyl)bis(propane-1,2-diol)

A 3-neck 250 mL round bottom flask equipped with a magnetic stirrer, nitrogen blanket, thermocouple controlled heating mantle and addition funnel is charged with PRIMENE™ TOA (a highly branched C8 tertiary alkyl primary amine available from Dow) (25 g, 0.19 mole, 1 equivalent). The addition funnel is charged with 96% pure Glycidol (35.2 g (32 mL), 0.48 moles, 2.5 equivalent) and added very slowly to the amine. The reaction is exothermic and therefore, slow addition of Glycidol and use of ice/water bath is used to control the reaction temperature not to exceed 65° C. The colorless reaction mixture turns viscous and yellow upon addition of the alkylene oxide. After the reaction is stirred for 6 hrs, GC indicates the presence of Glycidol and both the mono and bis products. At this point, the reaction mixture is heated at 70° C. for an additional 10 h until the mono adduct peak disappears. The reaction mixture is distilled to remove the excess Glycidol. The overall purity of the material is 96.4% and the overall yield of the distilled product is approximately 50 g (94%). The structure is confirmed by GC and NMR analysis. Retention time of the product is 24.78 min, [M+H]=278.1. NMR analysis is run in $CD_3OD$. $^1H$ NMR, (ppm):δ 1.012 (s, 9H), δ 1.226 (s, 2H), δ 1.459 (s, 6H), δ 2.430-2.934 (m, 4H), δ 3.468-3.725 (m, 6H). $^{13}C$ NMR (ppm), δ 38.14, 38.98, 39.66, 41.89, 42.47, 59.35, 65.28, 67.02, 70.65, 70.98, 75.87, 82.49 and 83.79.

The pK of the product is 9.0. Percent VOC measured on the crude amine sample according to ASTM D6886-rev is 3.6%, which is due to the impurities. 3,3'-((2,4,4-trimethylpentan-2-yl)azanediyl)bis(propane-1,2-diol) is retained in the column greater than 20 minutes and is therefore a zero VOC material according to ASTM D6886-rev protocol.

Example 2

The Paint Properties of 3,3'-((2,4,4-trimethylpentan-2-yl)azanediyl)bis(propane-1,2-diol) as Co-Neutralizer with NaOH (1:1) is Studied in the Following Formulation (Table 3)

TABLE 3

| Raw material | Supplier | Density, g/ml | Weight, g | Volume, ml |
| --- | --- | --- | --- | --- |
| Grind | | | | |
| Water | | 1.00 | 1.80 | 1.80 |
| Attagel 50 attapulgite clay thickener | Engelhard | 2.36 | 0.09 | 0.04 |
| Water | | 1.00 | 0.02 | 0.02 |
| Tamol 731A dispersant | Dow | 1.10 | 0.18 | 0.16 |
| Tergitol TMN-6, surfactant | Dow | 0.99 | 0.06 | 0.06 |
| Triton GR PG-70 | Dow | 1.08 | 0.06 | 0.06 |
| Drew Plus Y-381 defoamer | Drew Industrial | 0.87 | 0.06 | 0.07 |
| Neutralizer (amine) | | | 0.14 | 0.13 |
| Polygloss ™ 90 kaolin clay | KaMin | 2.60 | 1.05 | 0.40 |
| grind subtotal | | | | 2.73 |
| Letdown Masterbatch | | | | |
| Rhoplex VSR-2015 acrylic latex | Dow | 1.06 | 13.51 | 12.73 |
| Water | | 1.00 | 4.88 | 4.88 |
| Drew Plus Y-381 defoamer | Drew Industrial | 0.87 | 0.05 | 0.05 |
| Tiona 596 TiO2 slurry | Cristal Global | 2.35 | 8.40 | 3.58 |

TABLE 3-continued

| Raw material | Supplier | Density, g/ml | Weight, g | Volume, ml |
|---|---|---|---|---|
| Acrsyol RM-2020 NPR, rheology modifier (HEUR type) | Dow | 1.05 | 0.90 | 0.86 |
| Acrysol TT-935 rheology modifier (HASE type) | Dow | 1.06 | 0.18 | 0.17 |
| Formula total | | | 31.37 | 25.00 |

Table 4 has the summary of the paint data of 3,3'-((2,4,4-trimethylpentan-2-yl)azanediyl)bis(propane-1,2-diol)/NaOH (1:1) blend and comparing the properties of this blend with NaOH and Ammonia.

TABLE 4

| Properties | NaOH | Ammonia | 3,3'-((2,4,4-trimethylpentan-2-yl)azanediyl)bis(propane-1,2-diol) and NaOH (1:1) |
|---|---|---|---|
| pH | 8.9 | 8.8 | 9.1 |
| High-shear viscosity, 12,000 s$^{-1}$ (P) | 0.94 | 0.96 | 0.87 |
| Mid-shear viscosity, 57.4 s$^{-1}$ (cP) | 999 | 1010 | 645 |
| Gloss 60° | 60.49 | 59.12 | 71.75 |
| Hiding (S/mil) | 6.61 | 6.45 | 6.78 |
| Scrub Resistance (delta film thickness) | 0.66 | 0.49 | 0.54 |
| Wet Adhesion (Tape) - white % | 90% | 90% | 90% |

The data shows that the aminoalcohol/NaOH blend has better scrub resistance and significant improvement in 60° gloss compared to NaOH and ammonia alone. The gloss improvement indicates that the amino alcohol (3,3'-((2,4,4-trimethylpentan-2-yl)azanediyl)bis(propane1,2-diol) also enhances pigment dispersion.

The pH, viscosities, gloss, hiding, scrub resistance and wet adhesion of the formulations containing the tested compounds are determined as follows.

pH pH is measured using a basic pH meter (Denver instrument) at room temperature. The pH meter is calibrated by three buffer solutions (pH=4, 7 and 10) each time before measurement.

Viscosities

Viscosities are measured on an Anton Paar 301 rheometer at 25° C. using a 0.5 degree cone and plate geometry. A shear rate sweep from 0.5 to 12000 s$^{-1}$ is performed. High-shear viscosity is extracted at 12,000 s$^{-1}$ shear rate and mid-shear viscosity is extracted at 57.4 s$^{-1}$ shear rate.

Gloss

The Symyx coating station is used to coat 2"×2" coatings are coated on black/white Leneta chart by using a doctor blade set to a 6-mil gap. Gloss at 60° is measured on color gloss thickness instrument after coatings are dried in CTR (25° C.; 50% RH) for 7 days.

Hiding

The Symyx coating station is used to coat 2"×4" coatings on black release Leneta charts using a doctor blade set to a 3-mil gap. Reflectance, Y, is measured on color gloss thickness instrument after coatings are dried for 1 day. Using the hydraulic clicker-press and the 1"×2" die, the rectangular area is cut in the center of coating. The weight of the cut rectangle of coating is calculated by measuring the weight before and after peeling off coating. S/mil value is calculated from the Y reflectance value and coating thickness according to the Kubulka-Munk equation.

Scrub Resistance

The Symyx coating station is used to coat 1"×2"coatings on black scrub panels by using a doctor blade set to a 6-mil gap. Coatings are scrubbed at 624 rpm with 150 g weights for 4 cycles, totally 20 minutes. The change in coating thickness before and after scrubbing is measured.

Wet Adhesion

The Symyx coating station is used to coat 1"×2" coatings on green alkyd panels by using a doctor blade set to a 7-mil gap. 2×4 crosshatches are cut after the coatings are dried for 1 day. Coatings are soaked in water for 10 minutes and wiped dry using paper towel. Parmacel tape is immediately applied on the dried coatings. A rubber roller is rolled across the entire coatings ten times in order to apply even force, and the strips of tape are pulled off one by one quick and clean motion at 180 degree. The coatings are then scanned and analyzed using image analysis software to determine the percent white (paint) that remained in the crosshatch area.

Example 3

Synthesis, pKa, and VOC Evaluation of 2-((2-hydroxy-3-isopropoxypropyl)amino)-2-(hydroxymethyl)propane-1,3-diol A 250 mL round bottom flask equipped with a magnetic stirrer, nitrogen blanket and addition funnel is charged with tris(hydroxymethyl)aminomethane (54.45 g, 0.45 moles, 1.05 equivalent) and dissolved in 200 mL of water. Once all the amine dissolves, isopropyl methyl oxirane (50 g, 0.43 moles, 1.0 equivalent) is added slowly to the amine solution. The reaction is stirred at room temperature for 24 h and stopped after the GC records 90% conversion to the desired product. Alternatively, the reaction time can be reduced by heating up the reaction mixture to completion. The water and residual epoxide are removed by rotary evaporator. The overall purity of the product material is 91.3%, the rest being residual amine. The structure of the desired product is confirmed by GC-MS and NMR analysis. Retention time of the product is 24 min, [M+H]=238. NMR analysis is run in CD$_3$OD. $^1$H NMR (ppm): δ 1.04-1.67 (d, 2H), δ 2.63-1.79 (m, 2H), δ 3.29-3.66 (m, 15H). $^{13}$C NMR (ppm): δ 32.36, 55.41, 70.96, 72.77, 81.59, 82.13 and 83.47. The pKa value of the material is 7.8. Percent VOC measured on the crude amine sample according to ASTM D6886-rev is 8.7%, which is due to the residual amine (ret. time: 14 min). 2-((2-hydroxy-3-isopropoxypropyl)amino)-2-(hydroxymethyl)propane-1,3-diol is zero VOC according to ASTM D6886-rev protocol.

Example 4

2,2'-((2-Hydroxycyclohexyl)azanediyl)diethanol (DEA-CyHO)

A 500 mL 4-neck flask is equipped with a magnetic stirrer, a reflux condenser with nitrogen blanket, and a heating mantle with a temperature controller and a thermocouple. The flask is charged with 46.83 grams (0.48 moles) of cyclohexene oxide (CyHO) and 50.17 grams (0.48 moles) of diethanolamine (DEA). The mixture is heated to 60° C.

while stirring under nitrogen, and 10 drops of 80% 2-dimethylamino-2-methyl-1-Propanol (DMAMP-80™ from Dow) are added. The temperature of the reaction mixture is then increased to 75° C. After about 22 hours at 75° C., GC analysis shows the presence of 10% of DEA and 4% of CyHO. The temperature of the reaction mixture is then increased to 85° C. After about 6.5 hours at 85° C., GC analysis shows about 9% of DEA and about 1.3% of CyHO remaining. The reaction mixture is vacuum distilled using a Kugelrohr apparatus. GC analysis of the fraction distilling at an air bath temperature of 142-145° C. at 0.15 mmHg pressure shows >98% of CyHO-DEA. The yield is 78 grams (80%). $^1$H-NMR: 3.474-3.642 ppm, multiplet with intensity 5; 1.247-2.824 ppm, multiplet with intensity 12. $^{13}$C-NMR: 71.52 ppm, 63.67 ppm, 81.10 ppm, 36.62 ppm, 35.48 ppm; 34.38 ppm; 44.82 ppm; 78.36 ppm. EI GC/MS: m/e 172 (base), 158, 144, 100, 74, 56. FT/IR: 3353.7, 2930.4, 2858.8, 1654.8, 1451.8, 1405.8, 1365.5, 1331.8, 1282.3, 1253.5, 1203.7, 1160.8, 1116.5, 1074.7, 1035.3, 1002.4, 952.3, 930.9, 916.5, 866.5, 610.1, 562.2 cm$^{-1}$. pKa=8.6.

Example 5

1,1'-((1-Hydroxy-2-methylpropan-2-yl)azanediyl)bis (butan-2-ol) (AMP-2BO)

A 250 mL 3-neck flask is equipped with a magnetic stirrer, a reflux condenser with nitrogen blanket, and a heating mantle with a temperature controller and a thermocouple. The flask is charged with 35.79 grams (0.40 moles) of amino-2-methyl-1-propanol (AMP) and 72.25 grams (1.0 mole) of epoxy butane. The mixture is stirred under nitrogen at reflux for a total of 13.5 hours. The initial reflux temperature is about 70° C., and it slowly climbs to 105° C. by the end of the reflux period. GC analysis of the reaction mixture at the end of the reflux period shows the presence of epoxy butane, with the remainder being primarily AMP-2BO; little AMP-BO mono-adduct is detected. The reaction mixture is vacuum distilled using a Kugelrohr apparatus. GC analysis of the fraction distilling at an air bath temperature of 140-144° C. at 0.18-0.15 mmHg pressure showed >95% of AMP-2BO. The yield is 85.3 grams (91%). $^1$H-NMR: 0.958 ppm, triplet; 1.334-1.407 ppm, multiplet; 0.976 ppm singlet; 1.045 ppm, singlet; and 1.119 ppm, singlet, with combined intensity of 16; 3.182-3.509, multiplet with intensity 4; 2.346-2.708, multiplet with intensity 4. $^{13}$C-NMR: 20.51 ppm, 38.58 ppm, 39.01 ppm, 82.85 ppm, 83.93 ppm, 67.99 ppm, 69.22 ppm, 29.78 ppm, 32.44 ppm, 34.48 ppm, 79.53 ppm, 79.71 ppm, 69.55 ppm, 69.75 ppm. EI GC/MS: m/e 202, 174, 130, 102 (base), 84, 70, 55, 42. FT/IR: 3357.6, 2954.4, 2934.3, 2877.6, 1464.0, 1417.8, 1380.8, 1363.0, 1299.3, 1244.3, 1174.4, 1130.8, 1063.1, 982.6, 919.4, 862.9, 777.2, 735.5, 587.5 cm$^{-1}$. pKa=9.1.

Example 6

2-(Hydroxymethyl)-2-((2-hydroxypropyl)amino) propane-1,3-diol (TA-1PO)

A 500 mL 3-neck round bottom flask equipped with a thermocouple, magnetic stirring, nitrogen blanket and an addition funnel is charged with tris(hydroxymethyl)aminomethane (TA) (121 g, 1.0 mol) and water (200 g). The mixture is allowed to stir overnight resulting in a clear solution. The addition funnel is charged with propylene oxide (75 mL, 62 g, 1.07 mol) which is then added dropwise to the reaction mixture over 75 minutes. External cooling is used to maintain the reaction temperature below 30° C. during the addition. After stirring at RT for 24 hours, the mixture is warmed to 50° C. for 2 hours to ensure complete reaction. A GC sample indicates that 3.7% unreacted TA remains, 90.1% mono-adduct and 5.2% bis adduct forms. A GC/MS analysis of the product mixture verifies the identity of the desired mono-adduct with a molecular weight of 179. The pKa value is found to be 8.0, and the neutralization equivalent weight of the product mixture (48% solids) is 378.8.

Example 7

2-Ethyl-2-((2-hydroxybutyl)amino)propane-1,3-diol (AEPD-1BO)

A 500 mL 3-neck round bottom flask equipped with a thermocouple, magnetic stirring, nitrogen blanket and an addition funnel is charged 2-amino-2-ethyl-1,3-propanediol (119 g of 85% soln, 0.85 mol) and water (100 g). The mixture warms to 35° C. during the dilution step. The addition funnel is charged with butylene oxide (85 mL, 76 g, 1.05 mol) which is then added dropwise to the reaction mixture over 75 minutes. The reaction temperature remains below 35° C. during the addition. After stirring at RT for 24 hours, the mixture is warmed to 50° C.-60° C. for 12 hours to ensure complete reaction. A GC sample indicates that 0.7% unreacted AEPD remains, 86.9% mono-adduct and 7.0% bis adduct forms. A GC/MS analysis of the product mixture verifies the identity of the desired mono-adduct with a molecular weight of 191. The pKa value is found to be 8.7, and the neutralization equivalent weight of the product mixture (66% solids) is 340.7.

Example 10

Preparation of Paint Formulations Containing Aminoalcohols of the Invention

The paint formulations are prepared using F/T agent 1 as shown by structures below. The octanol water partition coefficient is calculated using the method of Moriguchi et al., Chem. Pharm. Bull. 40(1), 127-130 (1992). The calculated octanol-water partition coefficient for F/T-1 is 0.69. Table 5 shows the paint formulations used for the freeze-thaw experiments. Paint samples are frozen at −18° C. for 17 hours and then thawed at 25° C. for 7 hours. This constitutes 1 complete freeze-thaw cycle. Viscosities are measured after each freeze-thaw cycle using a Krebs Stormer Viscometer from Sheen at room temperature. The viscosity is measured in Krebs unit (KU). The results of freeze-thaw cycles on paint samples that contain a zero-VOC compound of the invention as a post-add are listed in the Table 6. The post-add compound is mixed at 2 wt % in the paint samples. The same paint formulation is used in preparing all the samples. The paint sample without any post-add is designated as "Blank."

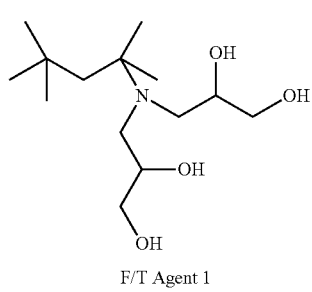 [SMILES: CC(C)(C)CC(C)(C)N(CC(O)CO)CC(O)CO]

F/T Agent 1

TABLE 5

| Ingredient | % by wt |
| --- | --- |
| Water | 17 |
| Kathon LXE | 0.1 |
| ROZONE 2000 | 0.3 |
| Tego Foamex | 0.02 |
| HEC | 0.5 |
| Orotan 731 A | 0.6 |
| AMP95 | 0.1 |
| Tergitol 15S40 | 0.2 |
| TiO$_2$ R 706 | 18.00 |
| Calcite MF | 4.00 |
| Omyacarb | 3 |
| ACRYSOL RM 5000 | 1 |
| AMP95 | 0.1 |
| Water | 16.16 |
| Tego Foamex | 0.02 |
| Water | 1.9 |
| ROPAQUE ULTRA E | 7.00 |
| PRIMAL ™ SF 018 | 30.00 |
| Total | 100 |

KATHON ™ LXE is an in-can, active biocide for preserving latex enamel paint formulations, and it is available from The Dow Chemical Company.
ROZONE ™ 2000 is a liquid fungicide and algaecide with broad-spectrum antimicrobial action for water- or solvent-based coatings, and it is available from The Dow Chemical Company.
TEGO FOAMEX ™ is a defoamer available from Evonik Industries.
HEC is hydroxy ethyl cellulose (NATRASOL 250 HBR Aqualon) available from Ashland.
OROTAN ™ 731 A is pigment dispersant for various latex based coatings. It is a sodium salt of a carboxylate polyelectrolyte, and it is available from The Dow Chemical Company.
AMP-95 is 2-amino-2-methyl-1-propanol with 5% water. It is a neutralizer and co-dispersant available from The Dow Chemical Company.
TERGITOL ™ 15S40 is a nonionic surfactant of a secondary alcohol ethoxylate available from The Dow Chemical Company.
TiO$_2$ R 706 is a multipurpose rutile titanium dioxide pigment available from DuPont.
CALCITE ME is of 10 micron particle size and available from 20MICRONS Ltd.
OMYACARB ™ is calcium carbonate is of particle size 2 microns and available from OMYA.
ACRYSOL ™ RM 5000 is a solvent-free, non-ionic associative thickening agent for use with latex paints. It is available from The Dow Chemical Company.
ROPAQUE ™ ULTRA E is an opaque polymer that increases the dry hiding capability of paint coatings, and it is available from The Dow Chemical Company.
PRIMAL ™ SF 018 is an acrylic polymer for use in paints to afford good abrasive scrub resistance. It is available from The Dow Chemical Company.

The KU values below 150 as reported in Table 9 are considered acceptable, and all the values (other than that for the Blank) reported are considered very acceptable.

TABLE 6

| Additive Name | wt % | Initial Viscosity (KU) | Viscosity after Freeze-Thaw cycles (KU) | | | | |
| --- | --- | --- | --- | --- | --- | --- | --- |
| | | | 1st cycle | 2nd cycle | 3rd cycle | 4th cycle | 5th cycle |
| F/T Agent 1 | 2% | 85.2 | 92.6 | 100.8 | 103.1 | 104.2 | 105.3 |
| Propylene Glycol | 2% | 89.8 | 101.3 | 103.2 | 115.1 | 99.4 | 98.2 |
| Diethylene Glycol | 2% | 91.0 | 101.1 | 105.1 | 106.9 | 100.6 | 98 |
| Blank | N/A | 90.9 | Fail | Fail | Fail | Fail | Fail |

The paint samples are subjected to paint performance testing. The paint samples that contain F/T Agent 1 when added as post-add survive five freeze-thaw cycles. The benchmarks used for the study are paint samples that contained propylene glycol, and diethylene glycol as freeze-thaw additives. The paint sample without any post-add is the "Blank." This sample fails the first cycle of freeze-thaw.

What is claimed is:

1. A compound of formula I:

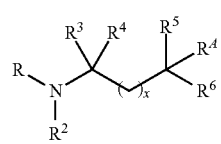

wherein x is 0, 1, or 2;
R$^A$ is OH or alkyl;
R is CH$_2$CHR$^1$OH, and R$^1$ is an unsubstituted alkyl, unsubstituted cycloalkyl, phenyl, phenyl-alkyl-, or alkoxyalkyl-, wherein the alkoxy group is 1 to 4 carbon atoms;
R$^2$ is H, alkyl, cycloalkyl, hydroxyalkyl, or independently R;
R$^3$ and R$^4$ are independently alkyl, cycloalkyl, phenyl, or hydroxyalkyl, or R$^3$ and R$^4$, together with the carbon to which they are attached, form cycloalkyl; and
R$^5$ and R$^6$ are independently H or alkyl, or R$^5$ and R$^6$, together with the carbon to which they are attached, form cycloalkyl,
or, when x is 0, R$^3$ and R$^5$, together with the carbon atoms to which they are attached, form cycloalkyl; and
provided that when x is 0, R$^A$ is OH and when x is 1 or 2, R$^A$ is alkyl.

2. The compound of claim 1 wherein x is 0 and R$^3$ and R$^4$ are independently hydroxyalkyl.

3. The compound of claim 1 wherein x is 0 and R$^3$ and R$^4$ are independently alkyl.

4. The compound of claim 1 wherein x is 0, R$^3$ is alkyl, and R$^4$ is hydroxyalkyl.

5. The compound of claim 1 wherein R$^5$ and R$^6$ are both H.

6. The compound of claim 1 wherein x is 0 and R$^3$ and R$^5$, together with the carbon atoms to which they are attached, form cycloalkyl.

7. The compound of claim 1 wherein x is 1 or 2 and R$^3$, R$^4$, R$^5$, and R$^6$ are independently alkyl.

8. The compound of claim 1 wherein R$^2$ is H.

9. The compound of claim 1 wherein R and R$^2$ are both CH$_2$CHR$^1$OH.

10. The compound of claim 1 is one of: 1,1'-((1-hydroxy-2-methylpropan-2-yl)azanediyl)bis(propan-2-ol); 1,1'-((1-hydroxy-2-methylpropan-2-yl)azanediyl)bis(butan-2-ol); 2-((2-hydroxybutyl)amino)-2-(hydroxymethyl)propane-1,3-diol; 2-(hydroxymethyl)-2-((2-hydroxypropyl)amino)propane-1,3-diol; 2-ethyl-2-((2-hydroxybutyl)amino)propane-1,3-diol; 2-((2-hydroxy-3isopropoxypropyl)amino)-2-methylpropane-1,3-diol; 2-((2-hydroxy-3-isopropoxypropyl)amino)-2-(hydroxymethyl)propane-1,3-diol; 2-(bis(2-hydroxybutyl)amino)-2-ethylpropane-1,3-diol; or 2-(bis(2-hydroxypropyl)amino)-2-ethylpropane-1,3-diol.

11. An aqueous based paint or coating comprising a binder, a carrier, a pigment, and an additive, wherein the additive is the compound of claim 1.

12. A compound of formula I:

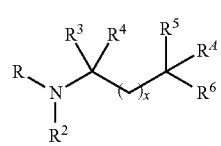

wherein x is 0;

$R^4$ is OH;

R is $CH_2CHR^1OH$, and $R^1$ is H, an unsubstituted alkyl, cycloalkyl, phenyl, phenyl-alkyl-, or alkoxyalkyl-, wherein the alkoxy group is 1 to 4 carbon atoms;

$R^2$ is alkyl, cycloalkyl, hydroxyalkyl, or independently R;

$R^3$ is H, cycloalkyl, phenyl, or hydroxyalkyl;

$R^4$ is alkyl, cycloalkyl, or phenyl, or $R^3$ and $R^4$, together with the carbon to which they are attached, form cycloalkyl; and $R^5$ and $R^6$ are independently H or an unsubstituted alkyl, or $R^5$ and $R^6$, together with the carbon to which they are attached, form cycloalkyl, or $R^3$ and $R^5$, together with the carbon atoms to which they are attached, form cycloalkyl.

13. The compound of claim 12, wherein R and $R^2$ are both $CH_2CHR^1OH$.

14. The compound of claim 13, wherein $R^1$ is H or an unsubstituted $C_{1-6}$ alkyl.

15. The compound of claim 12, wherein $R^3$ and $R^5$, together with the carbon atoms to which they are attached, form cycloalkyl.

16. The compound of claim 12, wherein $R^4$ is $C_{1-6}$ alkyl.

17. The compound of claim 12 is one of: 2,2'-((2-hydroxycyclohexyl)azanediyl)diethanol or 2-(bis(2-hydroxyethyl)amino)-2-ethylpropane-1,3-diol.

18. An aqueous based paint or coating comprising a binder, a carrier, a pigment, and an additive, wherein the additive is the compound of claim 12.

19. A compound that is 2,2'-((2-hydroxybutyl)azanediyl)diethanol.

20. An aqueous based paint or coating comprising a binder, a carrier, a pigment, and an additive, wherein the additive is the compound of claim 19.

* * * * *